United States Patent [19]
Block

[11] Patent Number: 5,632,736
[45] Date of Patent: May 27, 1997

[54] FLUID VOIDING APPARATUS

[76] Inventor: James C. Block, 4616 Moorland Ave., Edina, Minn. 55424

[21] Appl. No.: 608,758

[22] Filed: Feb. 29, 1996

[51] Int. Cl.⁶ .................................................. A61F 5/44
[52] U.S. Cl. .......................... 604/329; 604/352; 4/144.3; 206/363; 206/581
[58] Field of Search .................... 604/327–331, 604/352; 4/144.1–144.4; 206/363, 364, 438, 570, 581, 210

[56] References Cited

U.S. PATENT DOCUMENTS

| | | | |
|---|---|---|---|
| D. 302,042 | 7/1989 | McGovern et al. | D24/54 |
| 2,819,472 | 1/1958 | Sullivan | 4/110 |
| 2,878,486 | 3/1959 | Bartlett et al. | 4/110 |
| 3,005,992 | 10/1961 | Sullivan | 4/110 |
| 3,099,017 | 7/1963 | Sullivan | 4/110 |
| 3,163,868 | 1/1965 | Steel et al. | 4/110 |
| 3,306,515 | 2/1967 | Beaumont | 229/22 |
| 3,329,973 | 7/1967 | Bobbe | 4/110 |
| 3,535,714 | 10/1970 | Bjork | 4/112 |
| 3,579,653 | 5/1971 | Kuhn | 4/110 |
| 3,731,869 | 5/1973 | Griffin | 229/22 |
| 3,734,154 | 5/1973 | Polk | 150/9 |
| 3,964,111 | 6/1976 | Packer | 4/110 |
| 4,185,754 | 1/1980 | Julius | 206/210 |
| 4,197,849 | 4/1980 | Bostick | 128/295 |
| 4,198,979 | 4/1980 | Cooney et al. | 128/295 |
| 4,233,978 | 11/1980 | Hickey | 128/295 |
| 4,379,506 | 4/1983 | Davidson | 206/438 |
| 4,484,917 | 11/1984 | Blackmon | 604/327 |
| 4,568,339 | 2/1986 | Steer | 4/144.3 |
| 4,608,046 | 8/1986 | Towfigh | 604/329 |
| 4,681,573 | 7/1987 | McGovern et al. | 604/329 |
| 4,771,484 | 9/1988 | Mozell | 4/144.4 |
| 4,795,449 | 1/1989 | Schneider et al. | 604/329 |
| 4,804,377 | 2/1989 | Hanifl et al. | 604/352 |
| 4,815,151 | 3/1989 | Ball | 4/144.3 |
| 4,822,347 | 4/1989 | MacDougall | 604/329 |
| 4,911,698 | 3/1990 | Wapner | 604/329 |
| 4,917,238 | 4/1990 | Schumacher | 206/570 |
| 5,010,599 | 4/1991 | Niesson | 4/144.2 |
| 5,065,459 | 11/1991 | Tjahaja et al. | 4/144.2 |
| 5,091,998 | 3/1992 | Irazabal | 4/144.4 |
| 5,243,712 | 9/1993 | Cross | 4/144.2 |
| 5,285,532 | 2/1994 | Sealey | 4/144.3 |
| 5,370,637 | 12/1994 | Brodeur | 604/329 |

*Primary Examiner*—Robert A. Clarke
*Attorney, Agent, or Firm*—Merchant, Gould, Smith, Edell, Welter & Schmidt P.A.

[57] ABSTRACT

An extra-labia urine voiding apparatus including a container sized and shaped to externally cover a vulval region of a female anatomy. The container has an open side and defines a reservoir that is adapted for receiving urine. The container also includes a flange having a substantially planar surface adapted to face and generally surround a periphery of the vulval region. An extra-labia sealing structure is affixed to the planar surface of the flange. The sealing structure includes a pressure sensitive adhesive adapted to provide a generally fluid tight primary adhesive seal between the container and external tissue generally surrounding the vulval region. The voiding apparatus also includes a conduit in fluid communication with the reservoir of the container and adapted for draining urine from the reservoir.

7 Claims, 4 Drawing Sheets

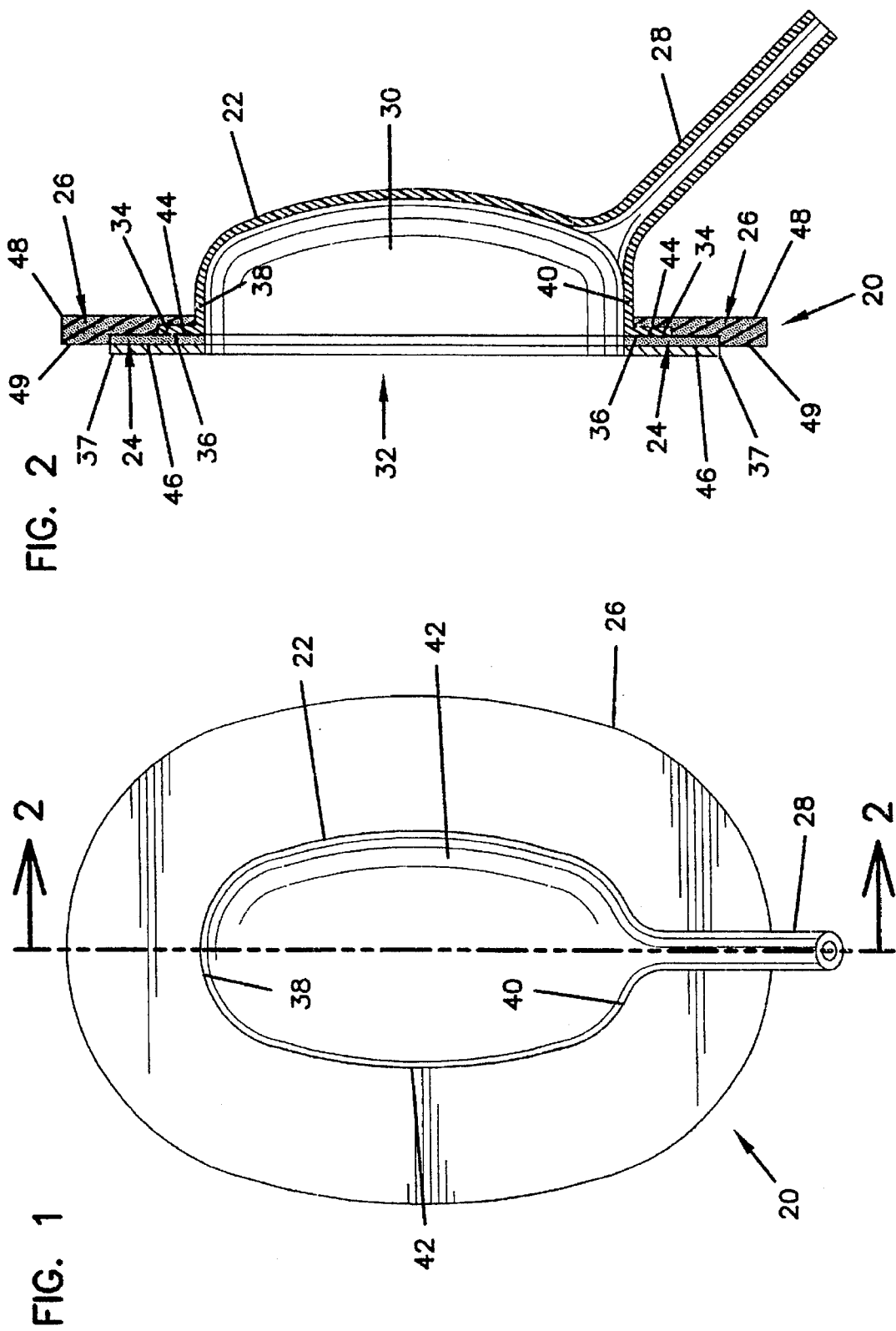

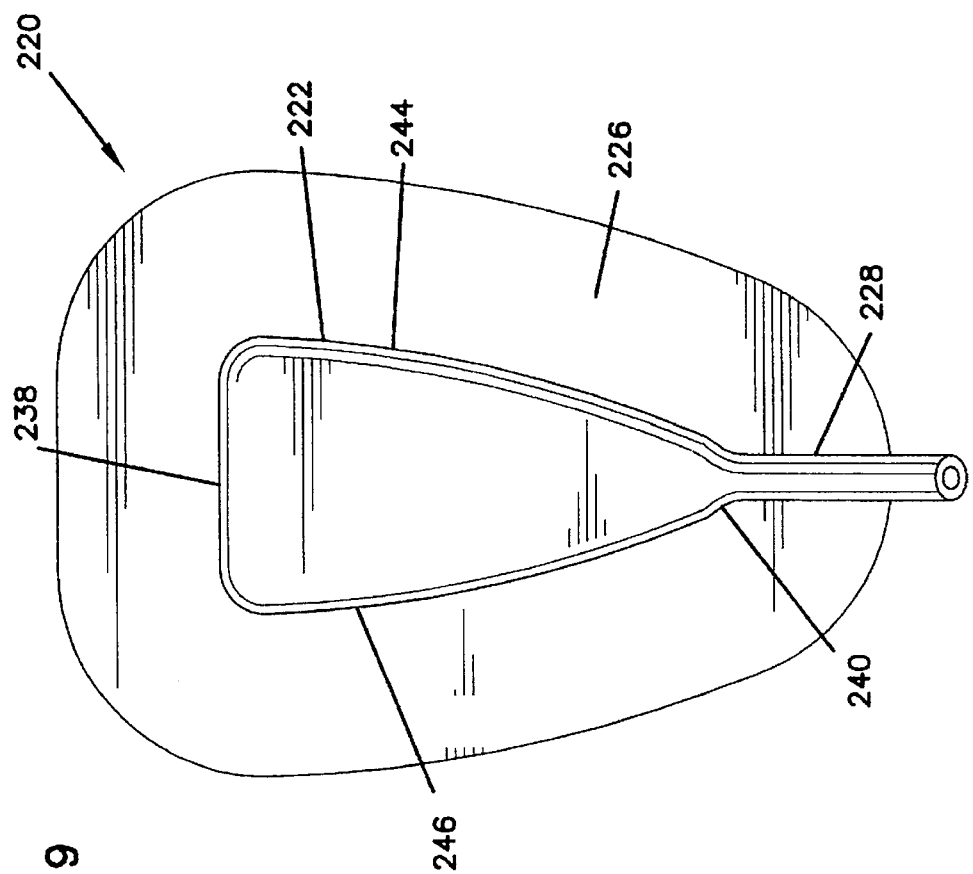
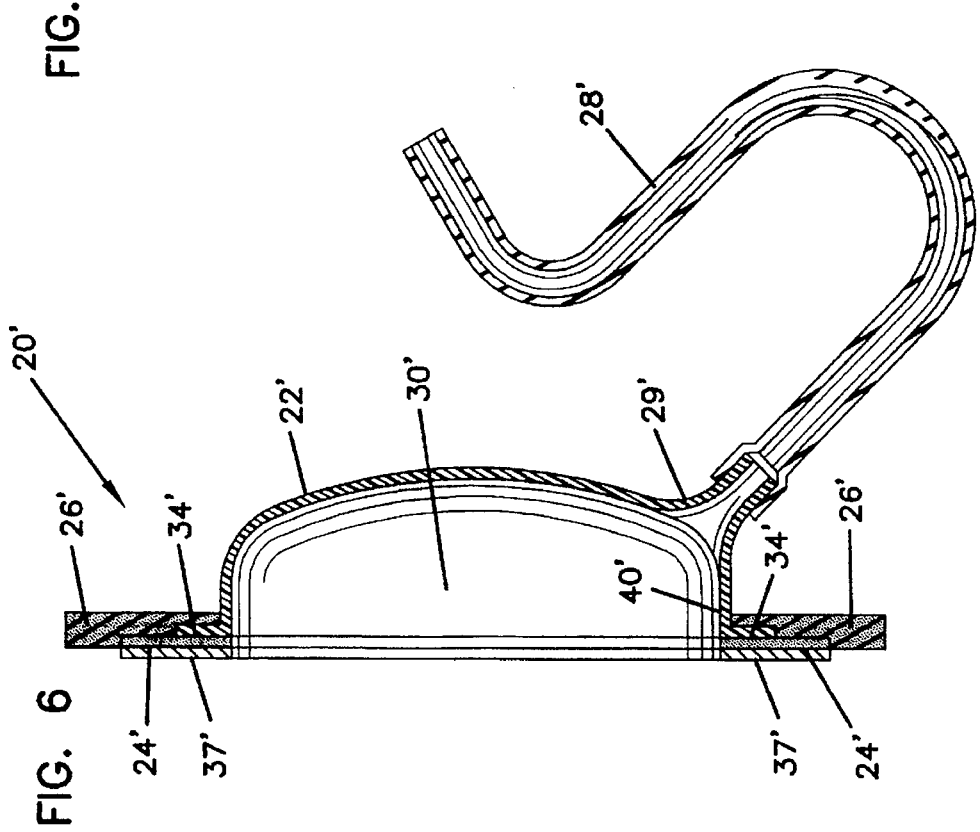

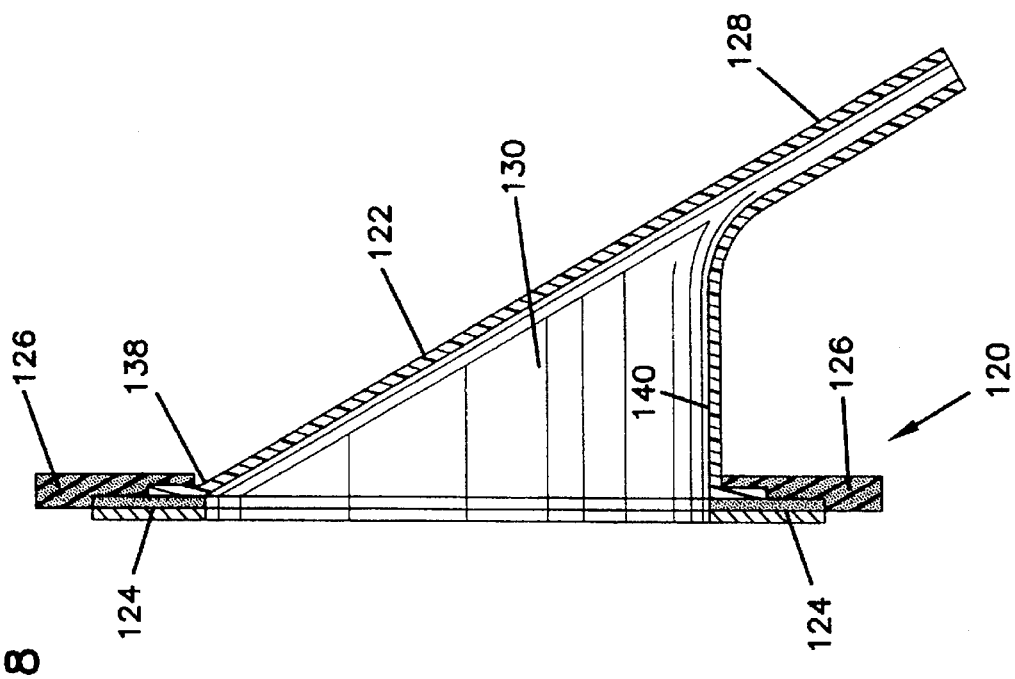
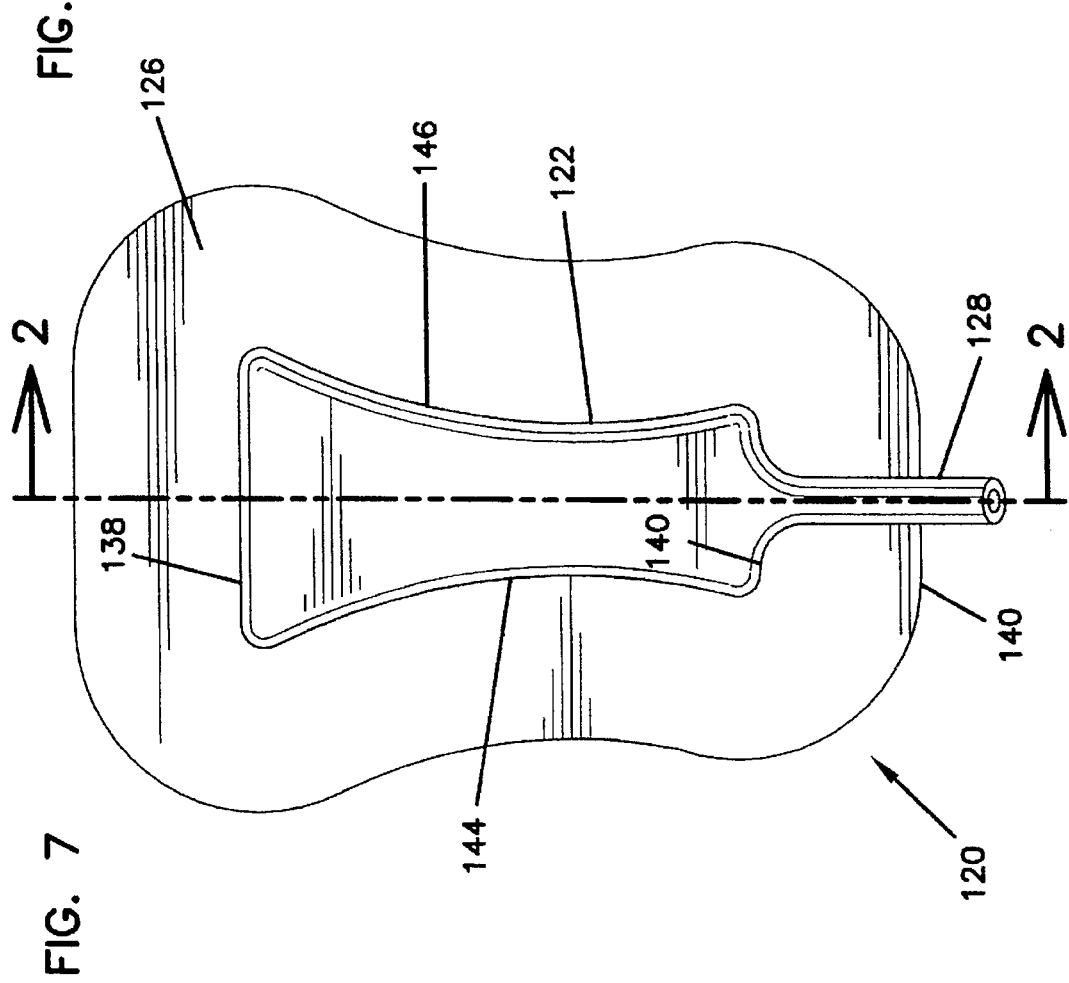

FLUID VOIDING APPARATUS

FIELD OF THE INVENTION

The present invention relates generally to fluid voiding apparatuses. More particularly, the present invention relates to extra-labia fluid voiding apparatuses.

BACKGROUND OF THE INVENTION

The prior art discloses a variety of sanitary devices that are designed to allow females to void urine while standing up in order to avoid non-hygienic contact with toilet facilities. Such devices often include substantially rigid funnel structures adapted to cover the vulval region of a female anatomy. However, such substantially rigid funnel structures are typically bulky, not readily disposable, and require a user to hold the funnel structure against the body during urination in order to maintain a fluid tight seal thereby increasing the possibility of misdirecting the urine from the end of the funnel.

U.S. Pat. No. 4,568,339 discloses a female incontinence device including a generally funnel shaped receiving member that defines a groove into which an adhesive paste is disposed to provide a seal to prevent urine leakage. The device can be reused by replacing the adhesive paste each time the device is used.

U.S. Pat. Nos. 4,484,917; 4,795,449; and 4,822,347 each disclose female incontinence devices having inter-labia adhesive sealing structures. Such incontinence devices are typically designed as catheters for long term use.

SUMMARY OF THE INVENTION

The present invention relates to an extra-labia urine voiding apparatus including a container sized and shaped to externally cover a vulval region of a female anatomy. The container defines a reservoir and includes an open side that is adapted for receiving urine into the reservoir. The container also includes a flange having a substantially planar surface adapted to face and generally surround a periphery of the vulval region. An extra-labia sealing structure is affixed to the planar surface of the flange. The sealing structure includes a pressure sensitive adhesive adapted to provide a generally fluid tight primary adhesive seal between the container and external tissue generally surrounding the vulval region. The voiding apparatus also includes a conduit adapted for draining urine from the reservoir.

It will be appreciated that in certain embodiments of the present invention, the extra-labia sealing structure may include an absorbent layer adapted to form a secondary mechanical seal that cooperates with the primary adhesive seal to prevent urine from leaking from the container. In alternative embodiments of the present invention, the pressure sensitive adhesive can be covered with a non-stick backing to facilitate storing and handling the urine voiding apparatus.

In other alternative embodiments, the pressure sensitive adhesive can have a predetermined bond strength corresponding to a predetermined voiding force to be exerted on the container. By matching the bond strength of the pressure sensitive adhesive to the anticipated voiding force exerted on the container, the pressure sensitive adhesive is adapted to maintain a generally fluid tight seal with respect to the vulval region without requiring manual assistance by a user of the voiding apparatus.

It will also be appreciated that urine voiding apparatuses constructed in accordance with the principles of the present invention can be incorporated within compact urine voiding kits that include absorbent material adapted for wiping the vulva region and packaging structure for containing the urine voiding apparatus and the absorbent material. Such a urine voiding kit can be easily carried in a purse.

It is an object of the present invention to provide an efficient urine conductor for use by females which is light weight and compact so that it can be carried in a purse while occupying a minimum amount of space. It is another object of the present invention to provide a urine conductor that is usable while disturbing a minimum amount of garb by the user. It is a further object of the present invention to provide a urine conductor for females that is sanitary and readily disposable after use. Also, it is an object of the present invention to provide a urine voiding apparatus that maintains a hands-free seal thereby reducing the possibility of soiling clothing through the misdirection of urine A variety of additional advantages and objects of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. A brief description of the drawings is as follows:

FIG. 1 shows a top-plan view of an extra-labia urine voiding apparatus constructed in accordance with the principles of the present invention;

FIG. 2 shows a cross-sectional view of a urine voiding apparatus of FIG. 1 taken along section line 2—2;

FIG. 6 shows a cross-sectional view of an alternative fluid voiding apparatus having a removable conduit;

FIG. 7 shows a top-plan view of an alternative fluid voiding apparatus constructed in accordance with the principles of the present invention and having a generally "waisted" platform;

FIG. 8 shows a cross-sectional view of the fluid voiding apparatus of FIG. 7 taken along section line 8—8; and FIG. 9 shows a top-plan view of an alternative fluid voiding apparatus constructed in accordance with the principles of the present invention and having a generally triangular platform.

DETAILED DESCRIPTION OF THE INVENTION

Reference will now be made in detail to exemplary embodiments of the present invention which are illustrated in the accompanying drawings. Wherever possible, the same reference numbers will be used throughout the drawings to refer to the same or like parts.

Figure 3:
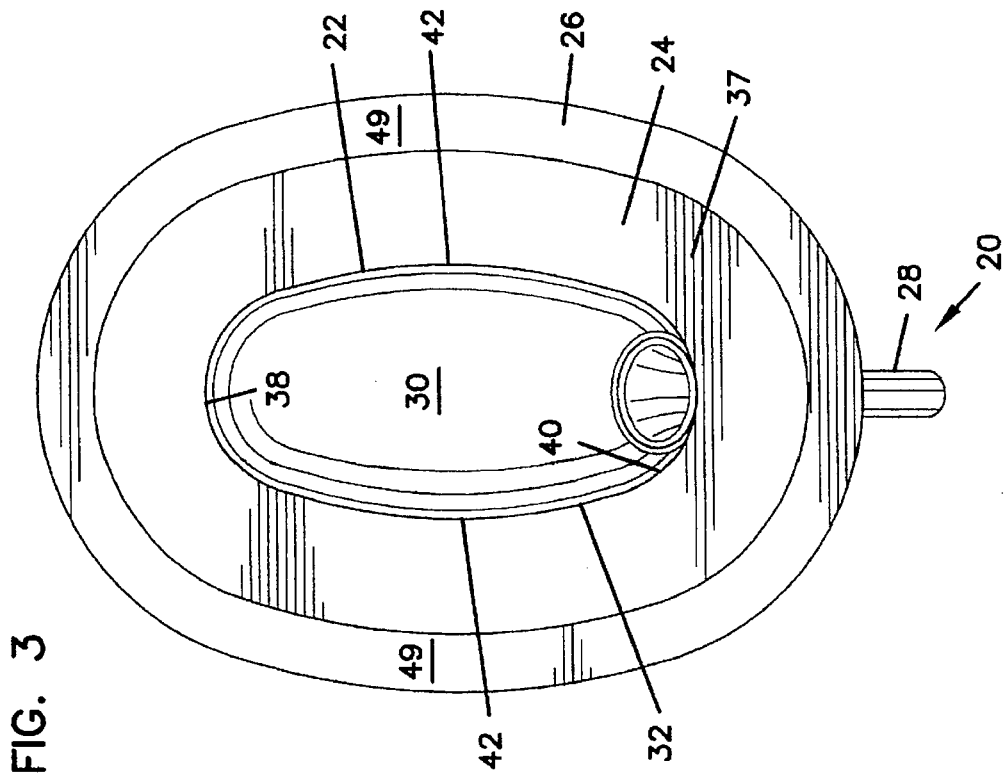
FIG. 3 shows a bottom-plan view of the fluid voiding apparatus of FIG. 1.

FIGS. 1–3 show a urine voiding apparatus 20 constructed in accordance with the principles of the present invention. In general terms, the urine voiding apparatus 20 includes a container 22 sized and shaped to cover a vulval region of a female anatomy. An extra-labia sealing structure such as a pressure sensitive adhesive 24 is connected to the container 22 and extends generally around a perimeter of an open side of the container 22. The pressure sensitive adhesive 24 is adapted for forming a generally fluid tight seal around a periphery of a user's vulval region. The extra-labia urine voiding apparatus 20 also preferably includes a layer of resilient material 26 connected to the container 22 generally adjacent to the pressure sensitive adhesive 24. The layer of resilient material 22 is arranged and configured to form a secondary mechanical seal or barrier that cooperates with the pressure sensitive adhesive 24 to prevent urine from leaking between the container 22 and a user's body. The urine voiding apparatus 20 preferably also includes a conduit 28 adapted for draining urine from the container 22.

The container 22 of the urine voiding apparatus 20 has a generally oval planform and defines a reservoir 30 adapted for receiving urine. The container has an open side 32 for allowing urine discharged from a user's urethral orifice to be received into the reservoir 30. The container 22 further includes a flange 34 surrounding a perimeter of the open side 32 of the container 22. The flange 34 includes a front side that has a substantially planar surface 36 adapted to face and generally surround a user's vulval region.

The container 22 includes a superior end 38 adapted to align generally with the mons Veneris of the female anatomy and an inferior end 40 adapted to align generally with the perineal region of the female anatomy. Extending between the superior end 38 and the inferior end 40 of the container 22 are opposing outwardly curved sides 42 that are arranged and configured to generally align along the labium majus of the female anatomy. The conduit 28 is integrally formed with the container 22 at a location generally adjacent to the inferior end 40 of the container 22.

It will be appreciated that the container 22 is preferably compact and constructed of a flexible material to facilitate carrying the urine voiding device in a purse. Exemplary construction materials include plastic, rubber and latex.

The pressure sensitive adhesive 24 of the urine voiding device 20 is preferably a double sided adhesive tape including a carrier film having opposing sides coated with adhesive. A portion of a first side 44 of the pressure sensitive adhesive 24 is affixed to the planar surface 36 of the container 34 such that the adhesive 24 extends completely around the perimeter of the open side 32 of the container 22. The remainder of the first side 44 of the pressure sensitive adhesive 24 preferably extends generally radially outward beyond the outer edge of the flange A second side 46 of the pressure sensitive adhesive 24 is adapted to provide a generally fluid tight primary adhesive seal between the container 22 and a user's external tissue generally surrounding the vulval region. The second side 46 of the pressure sensitive adhesive 24 is preferably covered with a non-stick backing 37, such as the backing conventionally used on stickers. The backing 37 prevents the second side 46 of the pressure sensitive adhesive 24 from adhering to objects when the urine voiding apparatus 20 is not being used.

It is preferred for the first side 44 of the pressure sensitive adhesive 24 to have a greater bond strength with respect to the carrier film than with respect to the external tissue surrounding the vulval region. Such a difference in bond strength causes substantially no adhesive residue to remain on the external tissue surrounding the vulval region. Additionally, the second side 46 of the pressure sensitive adhesive 24 is preferably permanently affixed to the planar surface 36 of the container 22 such that the adhesive 24 will not pull away from the container 22 when the voiding apparatus 20 is removed from the vulval region.

Although it is preferred for the pressure sensitive adhesive 24 to comprise a double sided tape, it will be appreciated that in certain embodiments a coating of pressure sensitive adhesive can be applied directly to the planar surface 36 without requiring a intermediate carrier medium as is commonly used in double sided tape.

The layer of resilient material 26 of the voiding apparatus 20 is preferably affixed to the portion of the first side 44 of the pressure sensitive adhesive 24 that extends radially beyond the flange 34 of the container 22. The layer of resilient material 26 preferably includes an outer portion 48 extending radially beyond the outer edge of the pressure sensitive adhesive 24. The outer portion 48 preferably has a sealing surface 49 that is substantially flush with respect to the second side 46 of the pressure sensitive adhesive 24. Alternatively, the sealing surface 49 could be offset with respect to the second side 46 so as to form a raised ridge surrounding the pressure sensitive adhesive 24. An inner portion of the resilient material 26 preferably extends behind the back of the flange 34 of the container 22.

It is preferred for outer portion 48 of resilient material 26 to completely surround the outer boundary of the pressure sensitive adhesive 24. It is also preferred for the resilient material 26 to be constructed of an absorbent material such as absorbent foam. However, the resilient material 26 may also be constructed of a non-absorbent elastomeric material such as rubber or plastic so as to form a gasket surrounding the pressure sensitive adhesive 24. Also, it will be appreciated that in certain embodiments of the present invention, the resilient material can be arranged so as to form a sealing surface along the inside edge of the pressure sensitive adhesive 24.

When the urine voiding apparatus 20 is placed over the vulval region of the female anatomy, the pressure sensitive adhesive 24 forms a generally fluid tight seal between the container 22 and external tissue generally surrounding the vulval region of a user such as the tissue of the mons Veneris, labium majus and the tissue of the perineum. While the first side 44 of the pressure sensitive adhesive 24 is affixed to the vulval region, the adhesive 24 holds the resilient material 26 against the external tissue surrounding the vulval region so as to form a secondary mechanical seal or barrier for preventing urine that leaks past the pressure sensitive adhesive 24 from soiling a user's clothing.

It will be appreciated that the volume of the reservoir 30 and the diameter of the conduit 28 can be varied to achieve a desired voiding pressure within the container 22. Additionally, various embodiments of the fluid voiding apparatus 20 can be constructed having pressure sensitive adhesives 24 of different adhesive bond strengths. The adhesive bond strengths will vary depending upon a variety of factors such as skin sensitivity, voiding pressures, the dimensions of the voiding apparatus 20, and the particular application. For example, a stronger adhesive bond strength will be required to provide a total hands-free seal as compared to an adhesive that is used to provide a manually assisted seal.

It will also be appreciated that the urine voiding apparatus 20 can be constructed in various sizes so that the proper apparatus can be chosen for a best fit. It will further be appreciated that the voiding apparatuses 20 of different sizes, shapes and adhesive bond strengths can be manufactured in different colors corresponding to a particular size or bond strength so as to color code the urinary voiding apparatuses 20.

Figure 4:
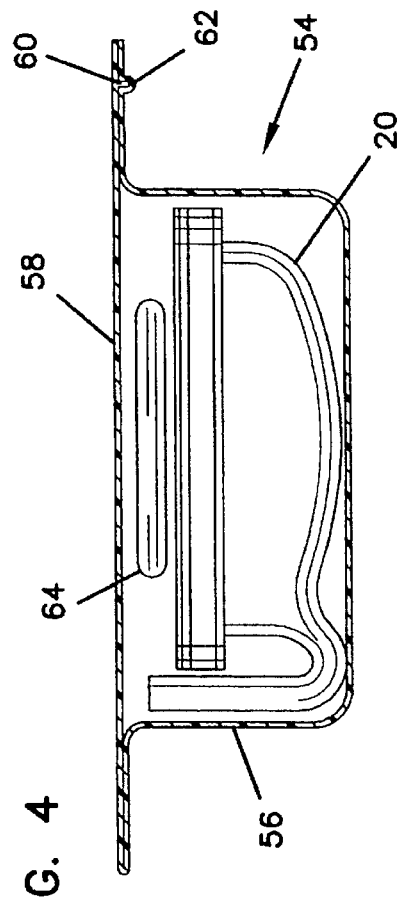
FIG. 4 shows a urine voiding kit constructed in accordance with the principles of the present invention.

FIG. 4 shows a urine voiding kit 54 incorporating the urine voiding apparatus 20. The kit 54 includes a packaging container 56 having a lid 58. The lid 58 has a tab 60 that frictionally engages a recess 62 defined by the container 56 such that the lid 58 can be opened and then resealed by pressing the tab 60 within the recess 62. Packaged within the packaging container 56 is the urine voiding apparatus 20 along with a piece of absorbent material 64 such as a napkin or tissue wipe adapted for wiping the vulval region after urination.

Figure 5:
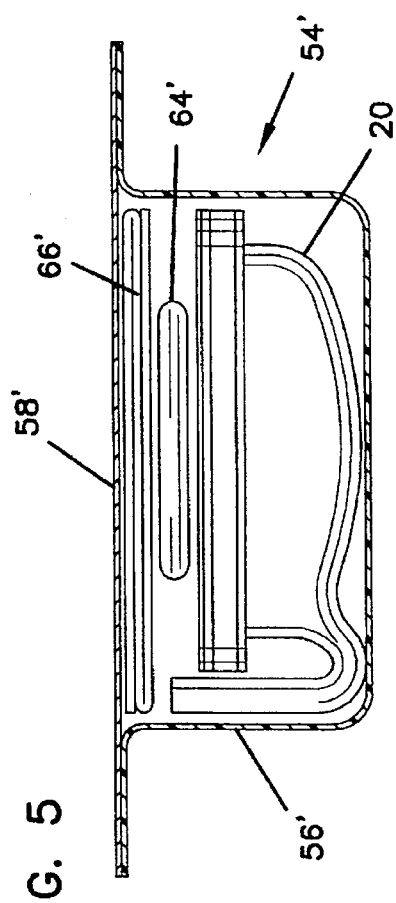
FIG. 5 shows an alternative urine voiding kit constructed in accordance with the principles of the present invention.

FIG. 5 shows an alternative urine voiding kit 54'. The kit 54' includes a packaging container 56' having a lid 58' that is non-resealably connected to the top of the container 56' by such conventional means as adhesive. The fluid voiding apparatus 20 is packaged within the packaging container 56' along with an absorbent wipe 64' Also contained within the packaging container 56' is a resealable bag 66' such as a conventionally known "ziplock" storage bag.

In practice, the kits of FIGS. 4 and 5 are preferably sized so as to be easily carried in a purse. In use, a female removes the urine voiding apparatus 20 from the sealed packaging container 56. The non-stick backing 37 then is removed from the pressure sensitive adhesive 24 thereby exposing the second side 46 of the pressure sensitive adhesive 24. The urine voiding apparatus 20 is then placed over the vulval region and the backside of the flange 34 is pressed toward the body to form a generally fluid tight adhesive seal between the first side 46 of the pressure sensitive adhesive 24 and the external tissue generally surrounding the vulval region. While the pressure sensitive adhesive 24 is bonded around the vulval region, the layer of resilient material 26 engages the vulval region to provide a secondary seal or barrier that cooperates with the adhesive 24 to prevent urine from leaking from the container 22. Urine is received in the reservoir 30 of the container 22 and directed away from the user's body through the conduit 28.

Because of the adhesive assisted seal, the user can focus attention on directing the urine travelling through the conduit 28 to a particular location, such as a toilet. After the voiding process is complete, the user removes the urine voiding apparatus 20 from the vulval region and dries the vulval region with the wipe 64. Finally, the wipe 64 and the urine voiding apparatus 20 are placed back in the packaging container 56 and the packaging container is resealed.

It will be appreciated that the urine voiding kit 54' is used in generally the same manner as the urine voiding kit 54. However, because the container 56' is not resealable, the urine voiding apparatus 20 and the wipe 64' are preferably sealed in the bag 66' after the voiding process is complete.

FIG. 6 shows an alternative urine voiding apparatus 20' constructed in accordance with the principles of the present invention. Similar to the urine voiding apparatus 20, the urine voiding apparatus 20' includes a container 22' defining a reservoir 30' configured for receiving urine. A pressure sensitive adhesive 24' is affixed to a flange 34' of the container 22' and extends generally around the periphery of the container 22' The urine voiding apparatus 20' also includes a layer of resilient material 26' adjacent to the pressure sensitive adhesive 24' and a non-stick backing 37' covering the pressure sensitive adhesive 24' Adjacent to an inferior end 40 of the container 22', the container includes an integrally formed spigot 29' in fluid communication with the reservoir 30' Removably mounted on the spigot 29' is a conduit 28' for directing urine away from the container 22' The conduit 28' is preferably press fit on the spigot 29'.

FIGS. 7 and 8 show an alternative urine voiding apparatus 120 constructed in accordance with the principles of the present invention. The urine voiding apparatus 120 includes a container 122 defining a reservoir 130 configured for covering the vulval region of a female anatomy so as to receive urine discharged from the urethral orifice. The container 120 has a superior end 138 adapted for alignment with the mons Veneris and an inferior end 140 adapted for alignment generally with the perineum. Extending between the superior and inferior ends 138 and 140 are a pair of sides 144 and 146 adapted to align generally along the labium majus. The sides 144 and 146 are inwardly curved such that the container 122 has a "waisted" or generally "hour-glass" shaped planform. A conduit 128 is integrally formed with the container 122 adjacent to the inferior end 140. The urine voiding apparatus 120 also includes pressure sensitive adhesive 124 and a layer or resilient material 126 that cooperate to provide a fluid tight seal between the container 122 and the vulval region of a female anatomy.

FIG. 9 shows another alternative urine voiding apparatus 220 constructed in accordance the principles of the present invention. The urine voiding apparatus 220 includes a container 222 adapted for covering the vulval region of a female anatomy. The container has a superior end 238 adapted to align generally with the mons Veneris and an inferior end 240 adapted to align generally with the perineum. Extending between the superior end and inferior ends 238 and 240 are opposing first and second sides 244 and 246 that are adapted to align generally along the labium majus. The first and second sides 244 and 246 tapered towards each other such that the superior end 238 is wider than the inferior end 240 and the container 222 has a generally triangular planform. The urine voiding apparatus 220 includes a pressure sensitive adhesive (not shown) and a layer of resilient material 226 such as foam that cooperate to provide a fluid tight seal between the container 222 and the vulval region of a female anatomy. The urine voiding apparatus 220 also preferably includes a conduit 228 integrally formed with the container 222 for draining urine from the container 222.

With regard to the foregoing description, it is to be understood that changes may be made in detail, especially in matters of the construction materials employed and the shape, size, and arrangement of the parts without departing from the scope of the present invention. It is intended that the specification and depicted embodiment be considered exemplary only, with a true scope and spirit of the invention being indicated by the broad meaning of the following claims.

What is claimed is as follows:

1. An extra-labia urine voiding apparatus comprising:

a container sized and shaped to externally cover a vulval region of a female anatomy, the container defining a reservoir and having a generally open side adapted for receiving urine into the reservoir, the container also including a flange forming a perimeter around the open side, the flange having a substantially planar surface constructed and arranged to face and generally surround a periphery of the vulval region;

an extra-labia sealing structure including a pressure sensitive adhesive affixed to the planar surface for providing a primary adhesive seal between the container and external tissue generally surrounding the vulval region, the sealing structure also including a layer of absorbent material affixed to the container generally adjacent to the pressure sensitive adhesive, the layer of absorbent material being arranged so as to extend generally around the perimeter of the open side of the container, wherein the layer of absorbent material is adapted to form a secondary mechanical seal that cooperates with the primary adhesive seal to prevent urine from leaking out of the container; and a conduit in fluid communication with the reservoir of the container, the conduit being adapted for draining urine from the reservoir.

2. The urine voiding apparatus of claim 1, wherein the pressure sensitive adhesive is covered by a removable non-stick backing.

3. The urine voiding apparatus of claim 1, wherein the layer of absorbent material comprises foam.

4. The urine voiding apparatus of claim 1, wherein the pressure sensitive adhesive has a predetermined bond strength corresponding to a predetermined voiding force to be exerted on the container, the pressure sensitive adhesive being adapted to maintain a generally fluid tight seal with respect to the tissue surrounding the vulval region without requiring manual assistance by a user of the voiding apparatus.

5. A urine voiding kit comprising:

an extra-labia urine voiding apparatus including:

a disposable container adapted to cover a vulval region, the container defining a reservoir adapted for receiving urine and including a flange having a substantially planar surface adapted to face and generally surround the vulval region;

an extra-labia sealing structure including a pressure sensitive adhesive affixed to the planar surface for providing a primary adhesive seal between the container and exterior tissue generally surrounding the vulval region, the pressure sensitive adhesive being covered by a removable non-stick backing, the sealing structure also including a layer of absorbent material affixed to the container generally adjacent to the pressure sensitive adhesive, the layer of absorbent material being arranged so as to extend generally around the perimeter of the open side of the container, wherein the layer of absorbent material is adapted to form a secondary mechanical seal that cooperates with the primary adhesive seal to prevent urine from leaking out of the container; and a conduit in fluid communication with the reservoir of the container, the conduit being adapted for draining urine from the reservoir;

a piece of absorbent material adapted for wiping the vulval region; and a packaging structure that contains the urine voiding apparatus and the piece of absorbent material.

6. The urine voiding kit of claim 5, further comprising a sealable bag contained within the packaging structure, the sealable bag being adapted for containing the urine voiding apparatus and piece of absorbent material after usage.

7. The urine voiding kit of claim 5, wherein the packaging structure is resealable.

* * * * *